United States Patent [19]

Roder

[11] 4,064,440
[45] Dec. 20, 1977

[54] X-RAY OR GAMMA-RAY EXAMINATION DEVICE FOR MOVING OBJECTS

[76] Inventor: Frederick L. Roder, 2425 Nottingham Drive, Falls Church, Va. 22043

[21] Appl. No.: 698,660

[22] Filed: June 22, 1976

[51] Int. Cl.² .............................................. G01N 23/02
[52] U.S. Cl. .................................... 250/359; 250/360; 250/367; 250/368
[58] Field of Search ............... 250/358 R, 358 T, 359, 250/360, 362, 367, 368, 445 T

[56] References Cited

U.S. PATENT DOCUMENTS

| 3,655,964 | 4/1972 | Slight ................................ 250/359 X |
| 3,766,387 | 10/1973 | Heffan et al. ........................ 250/360 |
| 3,808,437 | 4/1974 | Miyagawa et al. ............... 250/360 X |
| 3,808,444 | 4/1974 | Schneeberger et al. ........ 250/358 X |
| 3,944,833 | 3/1976 | Hounsfield ...................... 250/360 X |

Primary Examiner—Archie R. Borchelt
Attorney, Agent, or Firm—Nathan Edelberg

[57] ABSTRACT

This apparatus obtains information about the interior of optically opaque objects rectilinearly translated therethrough. This apparatus assures the conformity of objects to predetermined constraints for purposes of quality control, and enables content identification.

12 Claims, 2 Drawing Figures

4,064,440

X-RAY OR GAMMA-RAY EXAMINATION DEVICE FOR MOVING OBJECTS

GOVERNMENT USE

The invention described herein may be manufactured and used by or for the Government of the United States of America for governmental purposes without the payment to me of any royalty thereon or therefor.

BACKGROUND OF THE INVENTION

In order to determine the conformity of shape and composition of normally identical manufactured items and to identify unseen objects such as objectional items in luggage at an airport, it is often necessary to obtain more information concerning distribution of matter within the objects examined than is provided by conventional radiographs. The subject invention provides a means of obtaining this information for objects transported on a conveyor belt of similar rectilinear transport means. For example, conventional radiographic devices reveal the presence of voids in castings, but not their location. Similarly, while such devices reveal a pistol in luggage, they are incapable of revealing several types of bombs. This invention provides information which enables identification of a far wider variety of imperfections and items in opaque objects. This identification can be by visual inspection of a reconstructed image or by automatic analysis of a signal produced by the examined object having a detected deviation from a predetermined standard.

In prior devices, information concerning the distribution of matter, usually defects, has typicaly been obtained by stereo radiography. Using either an x- or gamma-ray source, film shadowgraphs are obtained for two orientations of the source and film relative to the object. These images are superimposed and the locations of the defects are obtained by noting the displacements of the defect images of known features. The determination may be made visually, with the aid of a stereo viewer, or analytically, by measuring displacements on the two shadowgraphs.

An extension of stereo radiography, termed longitudinal tomography, has been employed to image single planes within an object. Longitudinal refers to the orientation of the imaged plane relative to the long axis of the human body, which is the principal object examined. U.S. Pat. No. 2,400,516 to Kieffer teaches such a device. Also, "Tomosynthesis: A Three Dimensional Radiographic Imaging Technique: by D. G. Grant in the January 1972 issue of IEEE Transactions on Biomedical Engineering discusses such devices. A single film plate and, usually, an x-ray source are synchronously rotated about an object during exposure of the film such that one plane remains in focus while neightboring planes are blurred.

Recently, considerable advances have been made in examining opaque objects by computerized transverse axial tomography, referred hereinafter as CTAT. Transverse axial refers to the orientation of the imaged plane relative to the long axis of the human body. CTAT replaces film when a radiation-sensitive detector or detector array; images are constructed by a computer and, most often, diplayed on a cathode-ray tube. The source and detector are synchronously rotated through a semicircle about the object being examined. In presently available CTAT commercial equipment, a single detector and pencil-beam x-ray source are scanned across the object under examination for each orientation. Such devices are disclosed in U.S. Pat. No. 3,778,614 to Hounsfield. Also, the October 1975 issue of Scientific American has an article on CTAT and longitudinal tomography: "Image Reconstruction from Projections" by R. Gordon et al.

SUMMARY OF THE INVENTION

This invention is directed to apparatus that examines objects rectilinearly translated between x- or gamma-ray source and a plurality of radiation detectors. By translating the examined object, this apparatus enables continuous examination of any number of items instead of a singular object. This invention provides information while utilizing a fixed radiation source and detector array without utilizing film. It is capable of assuring quality control of nominally identical items on a conveyor belt, such as rocket motors, artillery shells, castings, and the like. It is also capable of identifying gross density distribution, a feature which enables the detection of irregularly shaped bombs, such as plastic bombs, in luggage.

In this specification, conveyor belt is understood to mean a rectilinear transport device upon which objects move at a constant velocity or at a velocity which may be independently monitored. Such belts are of continuous flexible material, of metallic sections, rollers, or overhead tracks with suspension means, or the like.

This apparatus is suitable for obtaining data for one transverse section, x-y plane, of examined objects and is readily expanded to give data in the third dimension, z, by extending the system vertically or by passing the objects through the same system repeatedly at different elevations.

It is, therefore, an object of this invention to provide information about the interiors of opaque objects moving on a conveyor belt.

Another object of this invention is to provide detection and location means for irregularities in production items on a conveyor belt.

Still another object of this invention is to provide detection means for items concealed within objects on a conveyor belt by density distribution techniques.

Yet another object of this invention is to provide detection and location means for voids in filling substances within metallic encasements on a conveyor belt.

A further object of this invention is to provide detection means for quality control of military explosive items on a conveyor belt.

A still further object of this invention is to provide detection means for plastic bombs in luggage or a conveyor belt.

These and other objects will become readily apparent from the specification and drawings in which:

DESCRIPTION OF THE PREFERRED EMBODIMENT

Figure 1:
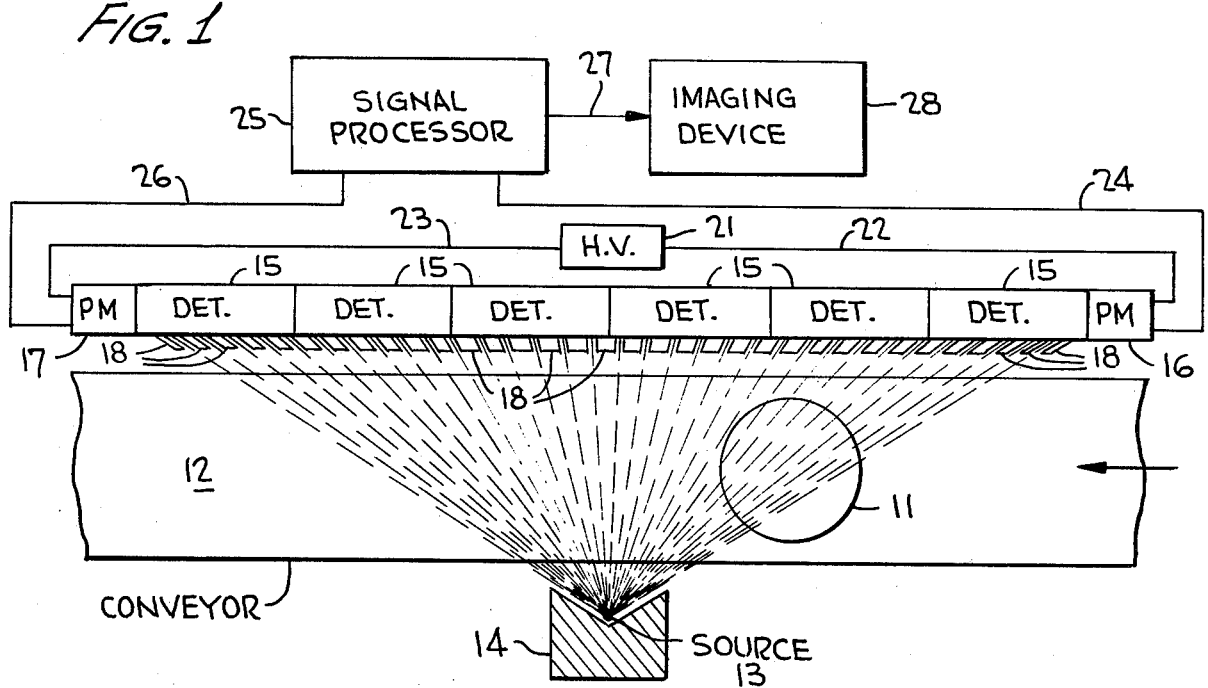
FIG. 1 is an overhead view of the apparatus of this invention with an array of detectors.

Turning now to the drawings, in FIG. 1, the object 11 to be examined is carried on a conveyor belt 12 past an angularly divergent x- or gamma-ray source 13. A combined shield and collimator 14 limits the field of radiation from source 13 to be directed only through the object 11 to an array of detectors 15, such as thallium-activated cesium iodide scintillators coupled to photomultipliers 16 and 17 at each end of the array. The optically coupled scintillators form a linear position-sensitive detector. The array 15 is also provided with a collimator 18 which establishes a path through which the photons can be directed to the detector means 15 from the source 13. Collimator openings for both source and detectors shall align and shall be coplanar with each other and define the plane to be examined. A high voltage power source 21 is connected through lead 22 to photomultiplier 16 and lead 23 to photomultiplier 17. The output of the photomultiplier 16 is connected through lead 24 as a first input to a signal processor 25. The output of Photomultiplier 17 is connected through a lead 26 as a second input to signal processor 25. In the signal processor 25, the information for the plane traversed by the radiation and detected by the plurality of detectors 15 is analyzed and information for a planar image is reconstructed and transmitted through lead 27 to an imaging device 28 on which a tomographic image is displayed.

Figure 2:
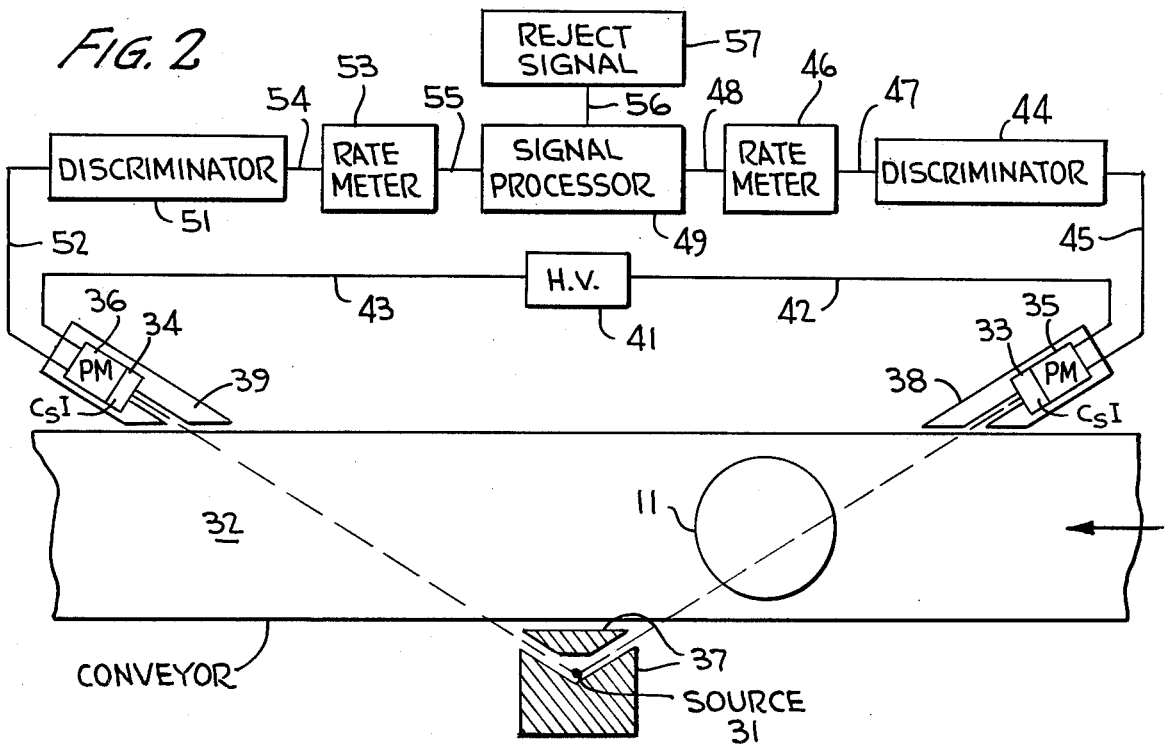
FIG. 2 is an overhead view of the apparatus of this invention with a pair of detectors.

The preferred embodiment as shown in FIG. 2 is characterized by: a single point gamma-ray source 31 such as a pellet of cobalt 60; a rectilinear transport device 32 such as a simple conveyor belt; a pair of photon detectors 33 and 34 such as three inch by three inch thallium activated cesium iodide scintillators coupled to photomultiplier tubes 35 and 36; a combination shield and colliminator 37 for the source; a combined shield and collimator 38 and 39 for each detector; a high voltage power supply 41 for the photomultiplier tubes 35 and 36; a lead 42 connecting photomultiplier 35 to said high voltage source 41 and a lead 43 connecting photomultiplier 36 to said high voltage source 41; a first discriminator 44 connected by lead 45 to said first photomultiplier 35, a first analog rate meter 46 connected by lead 47 to said first energy discriminator 44 and by lead 48 to a signal processor 49; a second discriminator 51 connected by a lead 52 to said second photomultiplier 36, a second anlog rate meter 53 connected by lead 54 to said second discriminator 51 and by lead 55 as a second input to said signal processor 49; and a lead 56 connecting the output of said signal processor to a reject signal means 57, which enables an unacceptable object 11 to be removed from the flow of items on conveyor belt 32. The signal processor has incorporated therein a reference of acceptable inputs applied thereto. In the event that the detected item 11 does not conform to the reference, the signal processor 56 will enable a reject routine that will isolate the unacceptable item 11 either by removing it from the conveyor belt to a reject status or by some marking means or the like. The openings in the collimator for both source 31 and detectors 33 and 34 are aligned and are coplanar with each other and define the plane to be examined.

The choice of source 13 or 31 is dependent upon the nature of the object 11 being examined and the rapidity with which the examination must be accomplished. In general, gamma-ray sources may more nearly represent point sources, are more stable, and provide a more convenient source of photons of energies above approximately two hundred kiloelectronvolts than do x-ray tubes. They are, therefore, the source of choice for applications wherein available and manageable activities provide a sufficient photon flux for an acceptably rapid examination. However, considerations of practicality often prohibit this condition from obtaining. In this case, an x-ray source, which may provide a considerably greater photon flux, must be employed. If an x-ray source is to be employed, it may be advisable to tailor the spectral content of the beam by filtering to limit total exposure to the objects under examination and to reduce so-called chromatic abberation, that is, spectral shifting of the transmitted flux due to the energy dependence of mass-attenuation coefficients. Since the lack of stability of x-ray sources may be a source of error, it may be necessary to instantaneously monitor the x-ray flux by means of an ionization chamber or similar radiation detector placed in the unattenuated radiation beam, either between the source and the object under examination or at an additional radiation port. The output from the detector would then be fed into the signal processor to normalize the signals obtained from detectors 15, or 33 and 34. The choice of x- or gamma-ray energy depends principally on two criteria: (1) that the attenuation length through the object under examination should be no more than several mean-free-paths in order to keep scattered radiation to an acceptable level and limit the dynamic range required of the detectors; and (2) that no higher energy than is needed be chosen to minimize exposure to operating personnel and, possibly, to the object under examination. A secondary criterion might be the atomic number at the region of principal interest within an object, $Z_1$, relative to that of the surrounding media, $Z_2$. If $Z_1$ is greater than $Z_2$, then a lower energy than would otherwise be determined might be desirable, and vice versa.

To extend the subject invention to simultaneously examine a multiplicity of planes within an object, a line gamma source may be substituted for the point source, with each segment of the line source collimated into a pencil beam. Conventional x-ray tubes are not well suited to examining a multiplicity of planes, although suitable x-ray sources may be cutsom fabricated with extended targets.

Choice of detector type and configuration is also a function of several parameters. For photon energies in excess of approximately two hundred kiloelectronvolts, scintillators such as NaI(T1) or CsI(T1) would probably be the detectors of choice. For lower photon energies, proportional counters or even ionization chambers would probably suffice. However, if extremely high count rates, say in excess of one million counts per second, are required, plastic scintillators may be necessary. For all but the thinnest objects examined, it will be necessary to collimate each detector or detector element such that a straight line to the source is defined. If a gamma-ray source is employed, a discriminator may be employed to accept only photons at the primary energy and thereby reject much the scattered radiation. A discriminator may also be useful if a carefully filered x-ray source is employed. In place of a discriminator, compound gas-filled detectors may be employed using the well-known techniques of K-edge filtering.

To examine a single plane in an object using the apparatus in FIG. 2, two discrete detectors will probably suffice in most cases. However, a third or even a fourth detector establishing an additional transmission path or paths, may supply a desirable redundancy of information in certain cases. To examine a multiplicity of planes within an object, using the apparatus in FIG. 2, the discrete detectors may be replicated vertically, or replaced by position-sensitive line detectors, such as delay-line proportional counters or long scintillation cylinders with photomultipliers at each end.

To examine a single plane using the apparatus shown in FIG. 1, either a linear array of discrete detectors or one or more position-sensitive line detectors will be required. To examine a multiplicity of planes, either (1) a two-dimensional array of discrete detectors, or (2) a multiplicity of position-sensitive line detectors, or (3) a position-sensitive two-dimensional detector, such as a multiwire proportional counter or an Anger Camera will be required.

In addition to the apparati shown in FIGS. 1 and 2, this invention may be embodied so that photons are transmitted through the conveyor belt, with the source positioned either above or below the belt. The source and the detectors are positioned so that the angular divergence of the detected radiation is maximized. For example, the angular divergence of the detected radiation from a point source located two inches from a conveyor belt twelve inches wide would be approximately one hundred twenty four degrees for an array of detectors sixty inches long located two inches from the opposite side of the conveyor. The center of the array would be directly opposite the source. In conventional radiographic procedures, the angular divergence of the radiation is minimized in order to approximate a parallel beam.

The apparatus of FIG. 1 will obtain the same data as is obtained by a conventinal CTAT scanner without rotating either the inspection system or the object being examined. In a conventional CTAT scanner, a scan at a selected angular orientation is completed before a scan at a succeeding angular orientation is initiated. In the subject invention, these data are obtained essentially simultaneously. A full data set is not available from the subject invention, since it is impossible to obtain data over a full one hundred eighty degree scan. This would require an infinitely thin object passing an infinitely long detector. However, the lack of a full data set results in somewhat poorer image resolution, rather than no image at all. Data obtained in this manner may be processed as is dicussed, for example, by Gordon et al., with the resultant image being displayed on a cathode ray tube or similar imaging device.

In FIG. 2, the subject invention can be used in a simplified form to detect perturbations in nominally identical objects under examination and also determine where in two dimensions these perturbations occur. The two discrete detectors 33 and 34 are located at what had been an end point of the array of detectors 15. A standard reference is incorporated into the signal processor 49. For checking for conformity to such standard, the response at each detector as a function of time as the object passes on the conveyor is known. If a defeat exists in the object 11, it will cause a perturbation in the response of each detector 34 and 33 as the defect intersects the line from the source to that detector. The location of the defect along this line may then be determined by noting the time delay between the occasion of the perturbations in the first and second detector responses. For example, if the two detectors are 60 inches apart and each is 33 inches from the source, then if the conveyor is moving at 5 inches per second and the defect is 4 inches from the source at the point of closest approach, then the second detector 33 will show a perturbation approximately 1.5 seconds after the first. Should the defect be 12 inches from the source at the point of closest approach, then the second detector 33 will show a perturbation approximately 4.5 seconds after the first 34. In the example of 105mm projectiles, the location of a defect in the x-y plane is of first importance because, even though a small defect in the steel case is acceptable, a small defect in the explosive fill cannot be accepted. Outputs from the detectors are provided to a signal processing unit 49, which may, in this case, be either an analogue or digital device. This unit determines the time relationship between detected perturbations and thereby establishes the locations of defects. The output may be in the form of a reject signal or a two-dimensional image of the standard on a cathode ray tube, or similar device, showing the location of defects as compared to the standard. The reject signal is produced by comparing the signals received from the detectors 34 and 33 with the standard to determine conformance. Failure of input signals to match the standard reference cause an output that can be a signal, an enabler for removal of the defective object, or any other known means of indicating a defective object.

It will be apparent that the embodiments shown are only exemplary and that various modifications can be made in structure and arrangement within the scope of the invention as defined in the appended claims.

What is claimed is:

1. In combination, means for transporting an object in a given direction at a known rate of travel along a selected rectilinear path having at least one substantially straight reference section;

an angularly divergent fan beam source of ionizing photons;

a plurality of photon detection means disposed in selected spaced relation and adapted to detect photons from said beam source;

said photon source and said photon detection means being disposed in the vicinity of said reference section such that an object transported by said means for transporting passes therebetween and photons of the angularly divergent beam of said photon source impinges upon said object, said angularly divergent beam photon source and said photon detection means having a fixed orientation with respect said reference section whereby the divergent beam of said photon source is aligned with the direction of travel of an object within said reference section and said detection means are spaced with respect said direction of travel;

a signal processing means, means connecting said detection means to said processing means, means for providing an output signal indicative of the mass distribution of said optically opaque object, and means connecting said processing means to said means, for providing an output signal.

2. The combination of claim 1 in which said photon source is substantially a point gamma-ray source, said means for limiting are combination shields and collimators, said detection means are at least two in number, said means for translating is a conveyor belt, said means for providing an output signal is a means enabling the isolation of a defective examined object, and wherein said signal processing means includes a standard reference for objects whereby a reject signal is produced when the information on an examined object differs from said reference.

3. The combination of claim 1 in which
said photon source is substantially a point gamma-ray source,
said means for limiting are combination shields and collimators,
said detection means is a linear array of detectors,
said means for translating is a conveyor belt, and
said means for providing an output signal is a means for generating and presenting a tomographic image.

4. The combination of claim 1 in which
said photon source is substantially a point x-ray source,
said means for limiting are combination shields and collimators,
said detection means are at least two in number,
said means for translating is a conveyor belt,
said means for providing an output signal is a means enabling the isolation of a defective examined object, and wherein
said signal processing means includes a standard reference for objects whereby a reject signal is produced when the information on an examined object differs from said reference.

5. The combination of claim 1 in which
said photon source is substantially a point x-ray source,
said means for limiting are combination shields and collimators,
said detection means is a linear array of detectors,
said means for translating is a conveyor belt, and
said means for providing an output signal is a means for generating and presenting a tomographic image.

6. The combination of claim 1 in which
said photon source is a sealed cobalt 60 gamma-ray source,
said detection means are at least two in number.
said means for translating is a conveyor belt,
said photon source is disposed to one side of said conveyor belt,
said detection means are scintillators disposed to the other side of said conveyor belt, and including a plurality of photomultiplier means of like number as said detection means,
means for optically coupling each of said detection means to one of each of said photomultiplier means, and
means for electrically coupling each of said photomultiplier means to said signal processing means.

7. The combination of claim 1 in which
said photon source is a sealed cobalt 60 gamma-ray source,
said detection means is a linear array of optically coupled scintillators,
said means for translating is a conveyor belt,
said photon source is disposed to one side of said conveyor belt,
said scintillators are disposed to the other side of said conveyor belt, and including
a pair of photomultiplier means,
one of said photomultiplier means optically coupled to one end of said array,
the other of said photomultiplier means optically coupled to the other end of said array, and
said means for providing an output signal is a means for generating and presenting a tomographic image.

8. A quality control tomographic examination device for the detection and location of density discontinuities in an optically opaque object moving therethrough comprising:
means for transporting said object in a given direction at a known rate of travel along a selected rectilinear path having at least one substantially straight reference section;
an angularly divergent fan beam source of ionizing photons;
at least two photon detection means disposed in selected spaced relation and adapted to detect photons from said beam source;
said photon source and said photon detection means being disposed in the vicinity of said reference section such that an object transported by said means for transporting passes therebetween and photons of the angularly divergent beam of said photon source impinges upon said object, said angularly divergent beam photon source and said photon detection means having a fixed orientation with respect said reference section whereby the divergent beam of said photon source is aligned with the direction of travel of an object within said reference section and said detection means are spaced with respect said direction of travel;
signal processing means;
means connecting said photon detection means to said signal processing means;
output means; and
means connecting said signal processing means to said output means, said signal processing means having an output representative of the time differential between signals produced in response to detection to density discontinuities in said object moving through said device at said selected rate of travel.

9. A tomograhic examination device as defined in claim 8 wherein said angularly divergent fan beam source is a point gamma-ray source and said photon detection means includes photon scintillator means with collimator input limiting means and photomultiplier output means.

10. A tomographic examination device as defined in claim 9 wherein said means for transporting is a conveyor belt means and said signal processor is adapted to produce an output representative of a selected deviation from said time differential when a plurality of like objects having a known density discontinuity are normally characterized by a prescribed time differential.

11. A tomographic examination device as defined in claim 10, wherein said point gamma-ray source is a directionally shielded and collimated cobalt 60 source.

12. A tomographic examination device as defined in claim 9 wherein said photon detection means incorporate an array of optically coupled scintillators disposed in juxtaposition with the array assembly in substantially parallel relation with respect said reference section.

* * * * *